(12) United States Patent
Zhu et al.

(10) Patent No.: US 7,693,665 B2
(45) Date of Patent: Apr. 6, 2010

(54) IDENTIFICATION OF MODIFIED PEPTIDES BY MASS SPECTROMETRY

(75) Inventors: Xiangping Zhu, Grafton, MA (US); Stephen J. Hattan, Roslindale, MA (US); Xunming Chen, Bedford, MA (US); Ioannis A. Papayannopoulos, Ashland, MA (US)

(73) Assignees: Applied Biosystems, LLC, Carlsbad, CA (US); MDS Inc., Concord, Ontario (CA)

( * ) Notice: Subject to any disclaimer, the term of this patent is extended or adjusted under 35 U.S.C. 154(b) by 1184 days.

(21) Appl. No.: 11/104,741

(22) Filed: Apr. 13, 2005

(65) Prior Publication Data

US 2005/0272164 A1 Dec. 8, 2005

Related U.S. Application Data

(60) Provisional application No. 60/561,938, filed on Apr. 14, 2004.

(51) Int. Cl.
*G06F 19/00* (2006.01)
*G01N 24/00* (2006.01)
*H01J 49/00* (2006.01)

(52) U.S. Cl. .......................... 702/19; 436/173; 250/281
(58) Field of Classification Search ........................ None
See application file for complete search history.

(56) References Cited

OTHER PUBLICATIONS

PCT International Search Report—Date of Mailing: Jan. 23, 2007.
Degnore JP et al. "Fragmentation of phosphopeptides in an ion trap mass spectrometer", Journal of the American Society for Mass Sepctrometry, vol. 9, No. 11, Nov. 1998, pp. 1175-1188.
Hogan JM et al. "Phosphorylation site identification via ion trap tandem mass spectrometry of whole protein and peptide ions: bovine alpha-crystallin A chain", Analytical Chemistry, vol. 75, No. 23, Dec. 1, 2003, pp. 6509-6516.
Jin Wen-Hai et al. "Phosphoproteome analysis of mouse liver using immobilized metal affinity purification and linear ion trap mass spectrometry", Rapid Communications in Mass Spectrometry, vol. 18, No. 18, Aug. 16, 2004, pp. 2169-2176.
Lee, CH et al. "On-membrane digestion of beta-casein for determinationo f phosphorylation sites by matrix-assisted laser desorption/ionization quadrupole/time-of-flight mass spectrometry", Rapid Communications in Mass Spec., vol. 15, No. 3, 2001, pp. 191-202.
Peters, EC et al. "Exploring the phosphoproteome with mass spectrometry", Mini Reviews in Medicial Chemistry, vol. 4, Mar. 2004, pp. 313-324.
Resing KA et al. "Mass spectrometric analysis of 21 phosphorylation sites in the internal repeat of rat profiliaggrin, precursor of an intermediate filament associated protein", Biochemistry, vol. 34, 1995, pp. 9477-9487.
Salek, M et al. "Analysis of protein tyrosine phosphorylation by nanoelectrospray ionization high-resolution tandem mass spectrometry and tyrosine-targeted product ion scanning", Analytical chemistry, vol. 75, No. 11, Jun. 1, 2003, pp. 2724-2729.
PCT Communication Relating to the Results of the Partial International Search (PCT/US2005/012347) mailed Sep. 1, 2006.
Annan, R.S. et al, "Phosphopeptide analysis by matrix-assisted laser desorption time-of-flight mass spectrometry", Analytical Chemistry, vol. 68, No. 19, Oct. 1, 1996, pp. 3413-3421.
Harvey, D.J. et al, "Relationship between in-source and post-source fragment ions in the matrix-assisted laser desorption (ionization) mass spectra of carbohydrates recorded with reflectron time-of-flight mass spectrometers", International Journal of Mass Spectrometry, vol. 188, No. 102, May 17, 1999, pp. 131-146.
Mann, M. et al, "Analysis of protein phosphorylation using mass spectrometry: deciphering the phosphoproteome", Trends in Biotechnology, vol. 20, No. 6, Jun. 1, 2002, pp. 261-268.
Muller D.R. et al, "Mass spectrometric characterization of stathmin isoforms separated by 2D page", Journal of Mass Spectrometry, vol. 34, No. 4, Apr. 1999, pp. 336-345.
Wirth, Urs et al, "Post-translational modification detection using metastable ions in reflector matrix-assisted laser desorption/ ionization-time of flight mass spectrometry", Proteomics, vol. 2, No. 10, Oct. 2002, pp. 1445-1451.

*Primary Examiner*—Lori A Clow (57) ABSTRACT

In various aspects, provided are methods for identification of the presence of modified peptides using at least in part mass spectrometric signals from metastable ions that are formed in the field free region of the analyzer. For example, in various embodiments where the modified peptides are phosphopeptides, such metastable ions can appear approximately 95 u lower than the precursor ion m/z value from which they were formed when the peptide contains a phosphate group. In various embodiments, detection of such metastable ions in a MALDI-TOF mass spectrum can identify the modified peptide. In various aspects, provided are methods for identification of the presence of modified peptides using at least in part MS/MS data from two or more of modified peptides, de-modified peptides and non-modified peptides by comparing the sequence and/or site of modification information for two or more of these three forms of a peptide.

7 Claims, 9 Drawing Sheets

SEQUENCE LISTING

<160> NUMBER OF SEQ ID NOS: 8

<210> SEQ ID NO 1
<211> LENGTH: 14
<212> TYPE: PRT
<213> ORGANISM: Artificial
<220> FEATURE:
<223> OTHER INFORMATION: synthetic peptide

<400> SEQUENCE: 1

Leu Gln Arg Gln Pro Ser Pro Ser Pro Gly Pro Thr Pro Arg
1               5                   10

<210> SEQ ID NO 2
<211> LENGTH: 17
<212> TYPE: PRT
<213> ORGANISM: Artificial
<220> FEATURE:
<223> OTHER INFORMATION: Synthetic

<400> SEQUENCE: 2

Arg Tyr Pro Arg Pro Val Pro Ser Val Pro Pro Ser Pro Ser Leu Ser
1               5                   10                  15

Arg

<210> SEQ ID NO 3
<211> LENGTH: 17
<212> TYPE: PRT
<213> ORGANISM: Artificial
<220> FEATURE:
<223> OTHER INFORMATION: synthetic peptide

```
<400> SEQUENCE: 3

Gly Thr Ser Phe Met Met Pro Thr Pro Tyr Val Val Thr Arg Tyr Tyr
1               5                   10                  15
Arg

<210> SEQ ID NO 4
<211> LENGTH: 18
<212> TYPE: PRT
<213> ORGANISM: Artificial
<220> FEATURE:
<223> OTHER INFORMATION: synthetic peptide

<400> SEQUENCE: 4

Cys Thr Asn Phe Met Met Pro Thr Pro Pro Tyr Val Val Thr Arg Tyr
1               5                   10                  15
Tyr Arg

<210> SEQ ID NO 5
<211> LENGTH: 20
<212> TYPE: PRT
<213> ORGANISM: Artificial
<220> FEATURE:
<223> OTHER INFORMATION: synthetic peptide

<400> SEQUENCE: 5

Asp Leu Asp Val Pro Ile Pro Gly Arg Phe Asp Arg Arg Val Pro Ser
1               5                   10                  15
Val Ala Ala Glu
            20

<210> SEQ ID NO 6
<211> LENGTH: 15
<212> TYPE: PRT
<213> ORGANISM: Bovine

<400> SEQUENCE: 6

Val Pro Gln Leu Glu Ile Val Pro Asn Pro Ser Ala Glu Glu Arg
1               5                   10                  15

<210> SEQ ID NO 7
<211> LENGTH: 17
<212> TYPE: PRT
<213> ORGANISM: Bovine

<400> SEQUENCE: 7

Tyr Lys Val Pro Gln Leu Glu Ile Val Pro Asn Pro Ser Ala Glu Glu
1               5                   10                  15
Arg

<210> SEQ ID NO 8
<211> LENGTH: 18
<212> TYPE: PRT
<213> ORGANISM: Bovine

<400> SEQUENCE: 8

Lys Tyr Lys Val Pro Gln Leu Glu Ile Val Pro Asn Pro Ser Ala Glu
1               5                   10                  15
Glu Arg
```

IDENTIFICATION OF MODIFIED PEPTIDES BY MASS SPECTROMETRY

CROSS REFERENCES TO RELATED APPLICATIONS

The present application claims the benefit of U.S. Provisional Application No. 60/561,938 filed Apr. 14, 2004. The entire contents of the foregoing provisional application are herein incorporated by reference.

INTRODUCTION

Mass spectrometry (MS), including MALDI-TOF MS, is a widely used analytical platform in numerous areas of biological research. Biomolecular samples (e.g., peptides, proteins, nucleic acids, carbohydrates) often contain moieties coupled to the biomolecule by labile chemical linkages that are susceptible to dissociation during analysis by the mass spectrometer. Such moieties are often of important significance in understanding the characteristics of the biomolecule and its relevance to the biological system under investigation. For example, proteins and or peptides containing phosphate linkages ($-PO_4$) are termed "phosphoproteins, phosphopeptides or phosphorylated peptides or proteins". These peptides and proteins are prime examples of biological molecules that are susceptible to dissociation of their phosphate group during MS analysis. The addition or subtraction of phosphate groups on proteins is widely used by biological systems as chemical signals or triggers for regulation of cellular processes, and, as such, identification of phosphoproteins is one example of significant interest in numerous areas of proteomic research. Likewise, other post-translational modifications of peptides such as glycosylation have important biological ramifications, and peptides that contain such modifications may also undergo dissociation of their glycosylated moiety. In this regard, methods that rapidly identify the presence of such potential group modification (such as phosphorylation and glycosylation) in peptide fragments prepared by enzymatic or chemical digestion of proteins, and selection of these peptides for further analysis by tandem mass spectrometry (MS/MS) techniques are highly desirable.

SUMMARY

The present teachings relate to a method for identification of modified peptides from mixtures of peptides when analyzed by mass spectrometry, e.g., axial matrix assisted laser desorption ionization (MALDI) time-of-flight (TOF) mass spectrometry.

In accordance with various aspects of the present teachings, methods for using the metastable behavior of labile biomolecules, such as a peptide that has a phosphate or sugar linkage, when analyzed by a mass spectrometer, such as a MALDI-TOF mass spectrometer, are provided that can be implemented as a means of detecting and identifying the labile biomolecule (e.g., phospho- and glyco-peptides). In various embodiments, the method includes identifying metastable ions from phosphopeptides (and/or glycopeptides and/ or other modified peptides) that are susceptible to post source decay in the field free region of a MALDI-TOF mass spectrometer.

In various aspects, methods of detecting and identifying the labile biomolecule (e.g., phospho- and glyco-peptides) are provided by generating a MS/MS spectrum of the labile biomolecule. In various embodiments, the method includes using tandem mass spectrometry to determine all or part of the sequence of a modified peptide and the site of modification based on searching a database using information from the sequence of the modified peptide, generating an MS/MS spectrum of a de-modified peptide that corresponds to the modified peptide and determining all or part of the sequence of the de-modified peptide and the site of modification based on searching a database using information from the sequence of the de-modified peptide. The sequence and the site of modification determined for the modified peptide to that determined for the de-modified peptide can be compared to identify that a modified peptide is present in a mixture of peptides if the sequence and the site of modification determined for the modified peptide substantially matches that determined for the de-modified peptide.

In various embodiments of the various aspects of the present teaching, a method of identifying the presence of a modified peptide, such as a post-translationally modified peptide, can be automated through the MS instrument software and facilitated by a computer algorithm that searches for and detects metastable ions in MALDI-TOF mass spectra that are collected in MS operation. Once identified, an experimentally derived mass unit value can be added to the detected metastable ion to identify the potential modified peptide, e.g., a potentially post-translationally modified peptide. In various embodiments, confirmation of the putative modified peptide can be carried out by tandem mass spectrometry techniques. Accordingly, in various aspects, the present teachings provide an article of manufacture where the functionality of one or more methods of the present teachings is embedded as computer-readable instructions on a computer-readable medium, such as, but not limited to, a floppy disk, a hard disk, an optical disk, a magnetic tape, a PROM, an EPROM, CD-ROM, or DVD-ROM.

These and other features of the present teaching are set forth herein.

BRIEF DESCRIPTION OF DRAWINGS

The skilled artisan will understand that the drawings, described below, are for illustration purposes only. The drawings are not intended to limit the scope of the present teachings in any way.

DESCRIPTION OF VARIOUS EMBODIMENTS

The present teachings provide a method of identifying the presence of various classes of biomolecules (e.g., peptides, proteins) that are modified in biological systems. For example, various constituents or moieties that modify biomolecules can have significant relevance to the state of the biomolecule and functional stability of the biological system to which the biomolecule pertains. In various embodiments for peptide identification, many of these moieties are linked to amino acid residues of peptides and proteins by labile chemical bonds that are susceptible to post source decay when analyzed by MS, such as in a MALDI-TOF mass spectrometer. The methods of the present teachings can be used with an axial MALDI-TOF MS such as the Voyager™ workstation (Applied Biosystems, Framingham, Mass.) or an axial MALDI-TOF-TOF MS instrument system such as the 4700 Proteomics Analyzer (Applied Biosystems, Framingham, Mass.).

In various embodiments involving MALDI-TOF MS analysis, biological samples of interest (e.g., peptides, proteins, nucleic acids, carbohydrates and the like) can be prepared by incorporation of the analyte sample into a solid phase matrix. The MALDI mass spectrometer instrument can use a specifically tuned laser to ionize the sample in a vacuum region called the MALDI source region. Liberated analyte ions, now in the gas phase, can be accelerated by application of an electrical potential to enter a field free region where they separate as a function of their mass to charge ratio and can thus be detected and categorized by this parameter. A phenomenon common to some ions with labile chemical linkages is dissociation into smaller ions in the field free region of the mass spectrometer in a process commonly known as "post source decay". As used herein, ions that dissociate in the field free region are termed metastable ions. These metastable ions in the field free region have the same velocity as the precursor ions from which they were formed, but possess lower kinetic energy due to their lower mass. Typically MS instrument acquisition parameters are specifically tuned for the maximum sensitivity and resolution for ions formed in the ion source region of the instrument. As a result, these ions are not focused to the same extent as the ions generated in the ion source region. Such lack of focusing of metastable ions results in a lower mass resolution as compared to the resolution of intact ions (or ions that dissociate in the ion source region) when detected, e.g., using a TOF analyzer. Another reason for the lower measured resolution of metastable ion fragments is that some of the chemical energy released during metastable ion formation is converted to kinetic energy in the fragment ions. Such increased kinetic energy typically does not change the average energy in the time-of-flight direction but can increase the energy spread of the fragment ions. Also since these fragments are formed outside of the ion source region, the application of delayed extraction techniques (which can impart velocity focusing properties) as described, e.g., in U.S. Pat. No. 5,627,369 do not operate on such fragment ions. Such metastable ions are usually detected in MALDI-TOF mass spectra that are collected in a reflector mode of operation of these analytical instruments.

In various embodiments, the methods of the present teachings can identify the presence of phosphopeptides. In various embodiments, these methods take advantage of the chemical lability of the phosphopeptides linkage, which results in dissociation of the phosphopeptide bond forming phosphoric acid and a lower mass peptide without its original phosphate group. This dissociation can take place, e.g., either in an ion source region after laser desorption/ionization or in a field free region of, e.g., a MALDI-TOF mass spectrometer. As used herein, the term de-phosphorylated peptide ions refers to ions that dissociate in the MALDI ion source region. Metastable ions generated in the field free region are not focused by the ion optics to the same extent as the ions generated in the ion source region resulting in lower mass resolution of these ions in TOF separation and ion detection. In various embodiments, we have observed that the metastable ions can be detected by a peak that is approximately 95 mass units (u) lower than the m/z value for the precursor ion from which it was generated. Identification of this metastable response in the MALDI-TOF reflector MS spectrum of a protein digest can be used to identify the presence of the putative phosphorylated peptide, i.e., as the peak that is about 95 u higher than the metastable ion and that has a substantially higher mass resolution than the metastable ion. The intact phosphorylated peptide can have a resolution that is substantially the same as the average resolution of other peptide peaks contained in the MALDI-TOF MS spectrum. However, metastable ions can have a resolution that is typically about 50% or lower than that of the average mass resolution over a given mass range. This observed mass difference (i.e., about 95 u) is not intuitive since the mass of a peptide which has lost its phosphate group should be theoretically 98 u lower than its phosphorylated counterpart and, indeed, this is the mass difference (−98 u) observed for phosphopeptides that dissociate in the ion source region of the MALDI-TOF mass spectrometer.

Figure 6:
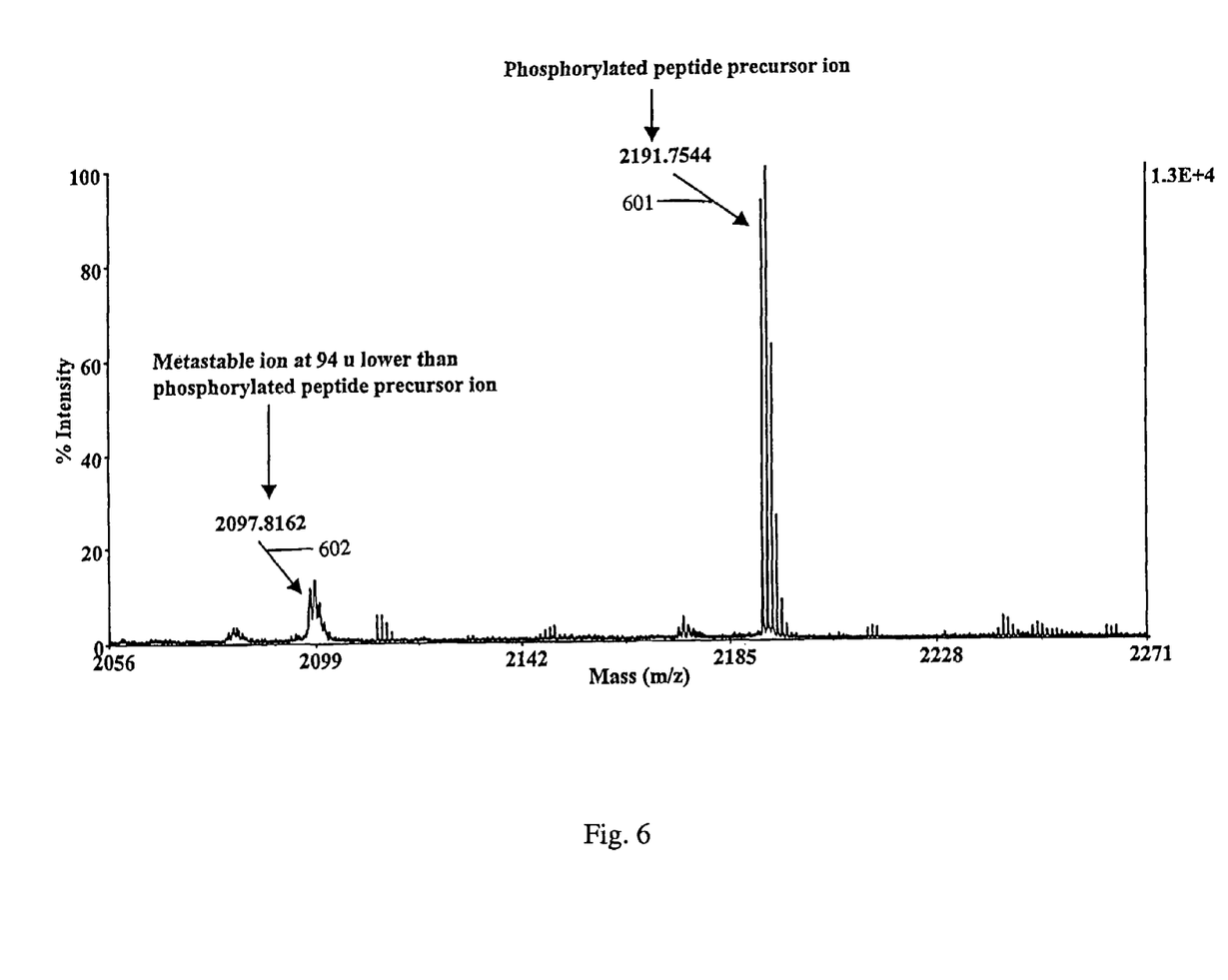
FIG. 6 depicts a MALDI-TOF spectrum for a synthetically pure phosphopeptide DLDVPIPGRFDRRVpSVAAE (SEQ ID NO: 5).

The value of mass difference between metastable ion and putative phosphopeptide (or other modified peptide) can be derived experimentally and can be dependent on instrument geometry. For example, analysis from reflector MS spectra collected on a 4700 Proteomics Analyzer from an LC MALDI study (in which 40 phosphorylated peptides were identified by the method of the present teachings) found the mass difference to be on average 95 u±1 u. In contrast when a Voyager DE™ STR (Applied Biosystems) instrument was used, the experimentally derived mass difference was found to be nominally 94 u (see FIG. 6).

We have discovered that the lower than expected m/z ratio difference of the metastable ion compared to its precursor phosphopeptide ion can be explained with reference to the design of a MALDI TOF instrument with an ion mirror (reflector) configuration. For this explanation, a reflector MALDI-TOF instrument can be thought of as having three distinct regions, a source region, a field free region and a mirror region. If we use $D_s$ for the length of the source region, $D_f$ for the length of the field free region, and $D_m$ for the length of the mirror region, then the time-of-flight in each region can be determined by the following:

$$t_s = \alpha \frac{2D_s}{\sqrt{V_s}} \sqrt{m} \quad (1)$$

$$t_f = \alpha \frac{D_f}{\sqrt{V_s}} \sqrt{m} \quad (2)$$

$$t_m = \alpha \frac{4D_m}{\sqrt{V_s}} \sqrt{m} \quad (3)$$

where $t_s$ represents the time-of flight within the source region, $t_f$ represents the time-of-flight within the field free region, $t_m$ represents the time-of-flight within the mirror region, $\alpha$ represents a constant, m represents the mass of the precursor peptide ion, and $V_s$ represents the source voltage.

Consider for example, metastable ions that are generated from a precursor peptide with a loss of mass, $\Delta m$ (98 u for phosphopeptide), in the field free region. The metastable ions fly with their precursor ions at substantially the same velocity until they reach the mirror region. Thus, the time-of-flight difference between metastable ions and precursor ions arises in the mirror region.

Up to the mirror, the metastable ion has the same initial velocity, but different mass from its precursor ion. The time it takes for the metastable ion to travel through the mirror region can be given by:

$$t_m^m = t_m \frac{m - \Delta m}{m} \quad (4)$$

where $t_m^m$ represents the time the metastable ion takes to travel through the mirror region.

The time t and mass m relationship is typically determined by that of the precursor peptide ion:

$$t = t_s + t_f + t_m = \alpha \sqrt{\frac{m}{V_s}} (2D_s + D_f + 4D_m) \quad (5)$$

or $$m = t^2 V_s / \left( \alpha^2 (2D_s + D_f + 4D_m)^2 \right) \quad (6)$$

The time-of-flight of the metastable ion can be expressed as $t^m = t - t_m + t_m^m$. According to equation (6), the observed mass, $m^m$, for the metastable ion can then be given by:

$$m^m = (t - t_m + t_m^m)^2 V_s / (\alpha^2 (2D_s + D_f + 4D_m)^2) \quad (7)$$

Rearranging and substituting yields the following relation:

$$m^m = m\left(1 - \beta \frac{\Delta m}{m}\right)^2 \quad (8)$$

$$\text{with } \beta \equiv \frac{t_m}{t} = \frac{4D_m}{2D_s + D_f + 4D_m} \quad (9)$$

Thus, the observed mass difference between the precursor peptide ion and its metastable counterpart ion can be given by:

$$m - m^m = 2\beta \Delta m - \beta^2 \frac{\Delta m^2}{m} \quad (10)$$

As described by Vestal et al. in J. Am. Soc. Mass Spectrom. 1998,9,892-911 ("Vestal"), which is hereby incorporated by reference herein, for a MALDI-TOF instrument with a single-stage source and mirror, the focusing condition can be given by the following condition:

$$D_f = 2D_s + 4D_m \quad (11)$$

Thus, $$\beta = \frac{2D_m}{D_f} \quad (12)$$

for such an instrument.

As taught by Vestal, high mass resolution can be achieved when $$\frac{4D_m}{D_f}$$

is in the range of 0.98 to 1, which corresponds to a $\beta$ in the range of 0.49 to 0.5. However, if one writes $D_m$ in terms of $D_f$ and $D_s$, a value for $\beta=0.5$ could correspond to an infinitely small source region, and thus could be a physically impractical value.

In various embodiments, a reasonable dimension would be a source region 5 mm long, a field free region 1000 mm long and a mirror length calculated according to equation (10). This ion optics configuration would have a $\beta$ that is 0.495.

For a phosphopeptide, $\Delta m = 98$ u. The experimentally observed mass difference between the metastable ion, $m^m$, and its precursor ion, m, can be derived using equation (10): $m - m^m = 95.3 \pm 0.7$ u, e.g., in the mass range of 1000 to 2500 u.

This derived value (previously referred to as the experimentally derived mass difference) represents the average observed mass difference over a given mass range and is substantially in accord with results observed experimentally. We refer to this derived value herein as the adjusted mass difference.

For different types of instruments, e.g., a different mirror length to drift tube length might be used, $\beta$ can be different, resulting in different observed metastable ion mass. For example, if $\beta$ is 0.49, the observed delta mass would be $m - m^m = 94.4 \pm 0.7$ u, e.g., in the mass range of 1000 to 2500 u.

Figure 5:
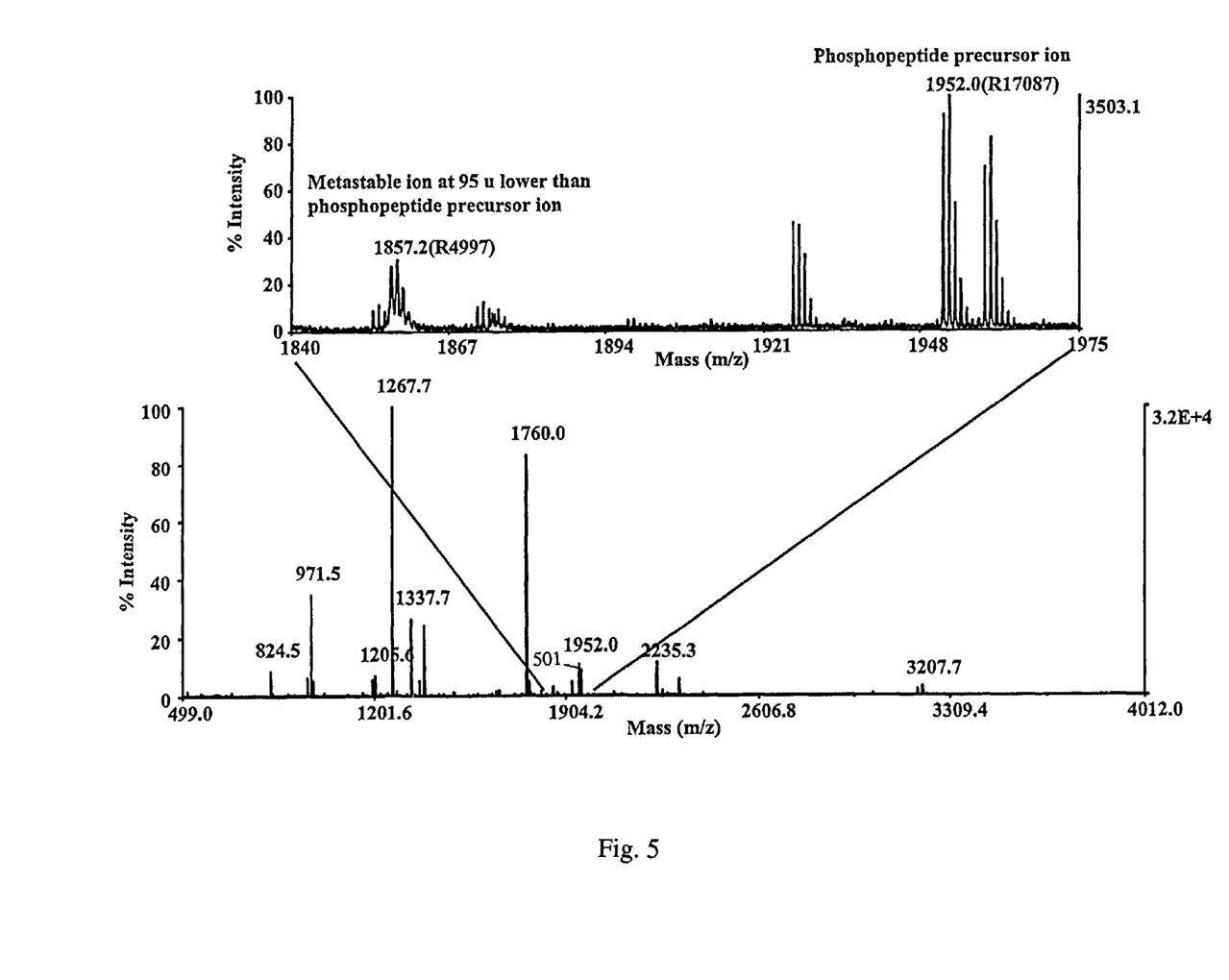
FIG. 5 depicts a MALDI-TOF-MS spectrum of an in-solution trypsin digest of a protein, α-casein, collected in reflector mode of operation of the MALDI-TOF analyzer. The upper panel is an expansion of the MALDI-TOF MS spectrum that visualizes the metastable ion used to identify the phosphopeptide precursor ion.

In various embodiments representing a typical workflow that can be carried out in accordance with the present teachings, a peptide MALDI sample can be prepared by mixing the sample with MALDI matrix such as α-cyano-4-hydroxycinnamic acid in a solution and then spotting the solution on a MALDI plate (MALDI target). After the solution is dried, the MALDI plate can be loaded into the ion source region of a MALDI TOF mass spectrometer. The MALDI TOF MS instrument can be run in MS only mode to generate a mass spectrum of the mixture of peptides having a plurality of peaks corresponding to the peptide ions over a range of massto-charge values. Typically data collection can be carried out in a reflector mode of operation to identify component masses (or component mass-to-charge ratios) in the sample due to higher resolution and higher mass accuracy measurements when the MALDI TOF MS instrument is operated in this mode. Using techniques known to those of skill in the art, the resolution of each of the peaks within the range of mass-to-charge values can be calculated by determining the mass value at the peak divided by the width of the peak (measured at 50% of the peak intensity). From the individual resolutions, the average mass resolution for the peptide peaks over a given mass range can be determined. One or more of the peaks in the mass spectrum with a resolution substantially lower than the average resolution of the identified peaks (see, for example, FIGS. 2, 5 and 6) can be selected as a putative metastable ion of an intact peptide precursor ion. The adjusted mass difference (e.g., 95 u in this example for phosphorylated peptides) can be added to the mass-to-charge value of the selected putative metastable peak to determine whether or not a peak exists in the spectrum at the newly calculated mass-to-charge value. If such a peak exists, it can be identified as a phosphopeptide precursor ion. The foregoing workflow can be repeated to identify the presence of other putative phosphopeptides present in the spectrum. According to the questions being addressed by the MS analysis, the data derived from collection of the MS spectra can be used for protein identification through protein database search of peptide mass fingerprinting (PMF) or the data can be used for the selection of precursor ions for further experiments such as, for example, using tandem mass spectrometry (MS/MS) to identify proteins or to confirm the phosphopeptide identified in accordance with the present teachings is indeed a phosphopeptide. In various embodiments, the instrument for conducting MS/MS analysis is an Applied Biosystems 4700 Proteomics Analyzer, but other tandem MS instruments can be used also.

In various embodiments, the functionality of one or more of the methods of the present teachings described herein is implemented as computer-readable instructions on a general purpose computer. The computer can be separate from, detachable from, or integrated into a mass spectrometry system. The computer-readable instructions can be written in any one of a number of high-level languages, such as, for example, FORTRAN, PASCAL, C, C++, or BASIC. The computer-readable instructions can be written in a script, macro, or functionality embedded in commercially available software, such as EXCEL or VISUAL BASIC. The computer-readable instructions could be implemented in an assembly language directed to a microprocessor resident on a computer. For example, the computer-readable instructions could be implemented in Intel 80×86 assembly language if it were configured to run on an IBM PC or PC clone.

In various embodiments, the computer-readable instructions can be embedded on an article of manufacture including, but not limited to, a computer-readable program medium such as, for example, a floppy disk, a hard disk, an optical disk, a magnetic tape, a PROM, an EPROM, CD-ROM or DVD-ROM. As used herein, the terms "algorithm" and "computer algorithm" refer to computer-readable instructions.

In various embodiments, the methods of the present teachings can be performed by the MALDI-TOF MS instrument software using a computer algorithm that implements one or more methods of the present teachings to detect and identify peptide peaks that are modified with functional groups that undergo facile cleavage when analyzed by the MALDI-TOF mass spectrometer. For example, in various embodiments, an algorithm implements a method of the present teachings that uses the following strategy to identify metastable ions that define the presence of post-translationally phosphate modified peptides in complex mixtures such as are generated when mixtures of proteins are digested with, e.g., enzymes (such as trypsin, chymotrypsin, lysine endopeptidase, ARG-C, ASP-N, V8, or other enzymes known to those of ordinary skill in the art), chemical reagents (such as cyanogens bromide or the like), or combinations thereof, in proteomics experiments to facilitate protein identification and characterization. The mass resolution of the peaks in the mass spectrum (e.g., generated in linear mode, reflector mode, etc.) can be determined by MALDI TOF instrument software across a portion or the whole mass range. Peaks of lower resolution than values measured for typical peptide responses are identified as potential derivatives of phosphopeptides and stored in memory. For example, the algorithm can be set to identify peaks as putative metastable ions with resolutions ranging from 3,000 to 6,000 depending on instrument tuning conditions. Subsequently ions having m/z values 95 u greater than the detected ion of low resolution stored in the previous step and also having a resolution that is consistent with the mass resolution for peptides analyzed by MALDI-TOF MS (typically >10,000) are identified and stored as being predicative of potential phosphopeptides. Ion signals selected by this approach represent putative phosphopeptides in the analyzed mixture. Further confirmation of this prediction can be accomplished by further analysis of the putative phosphopeptide by tandem mass spectrometry (MS/MS) such as, but not limited to, MALDI-TOF-TOF-MS analysis.

In various embodiments, a method of the present teachings can be used with a wide variety of workflows as set forth in detail below. For example, various embodiments of the methods of the present teachings can also be used with either a protein-based or peptide-based workflow.

In various embodiments, protein mixtures that contain phosphoproteins can be separated by SDS polyacrylamide gel electrophoresis (SDS-PAGE). Bands from gel electrophoresis separation of the protein mixture can be excised and proteins contained therein digested by an in-gel (in-situ) enzymatic or chemical digestion strategy. Peptide mixtures that result from such digestion are analyzed by mixing the peptide mixture (sample) with matrix (such as alpha-cyano-4-hydroxycinnamic acid, 2,5-dihydroxybenzoic acid, sinnapinic acid or the like), dried and analyzed by MALDI-TOF-MS. One or more methods of the present teachings is then applied to identify putative phosphopeptides.

In various embodiments, protein mixtures that contain phosphoproteins can be separated by SDS polyacrylamide gel electrophoresis (SDS-PAGE). Bands from gel electrophoresis separation of the protein mixture can be excised and proteins contained therein digested by an in-gel (in-situ) enzymatic or chemical digestion strategy. Liberated peptide mixtures can be further separated by high performance liquid chromatography (HPLC) methods such as, e.g., one dimension reversed phase, multiple dimensions in which two or more orthogonal dimensions of separation can be coupled to separate such complex mixture of peptides, and combinations thereof. Ultimately, separated peptide mixtures are co-deposited with a MALDI matrix onto a MALDI plate, or directly mixed with MALDI matrix, and deposited onto a MALDI plate. Resultant samples are analyzed by MALDI-TOF-MS. One or more methods of the present teachings is then applied to identify putative phosphopeptides.

In various embodiments, protein mixtures that contain phosphoproteins can be separated by SDS polyacrylamide gel electrophoresis (SDS-PAGE). Resultant gels can be probed using a molecular scanner approach. By this approach proteins are electroblotted through a membrane that is impregnated with an enzyme (such as trypsin or the like). As the proteins transverse the enzyme membrane they are digested into peptides, which are subsequently captured on a peptide capture membrane. Subsequently the peptide capture membrane is sprayed with a MALDI matrix (such as alpha-cyano-4-hydroxycinnamic acid, 2,5-dihydroxybenzoic acid, sinnapinic acid or the like), dried and analyzed by MALDI-TOF-MS. One or more methods of the present teachings is then applied to identify putative phosphopeptides.

In various embodiments, protein mixtures that contain phosphoproteins can be digested with an enzyme (such as trypsin, chymotrypsin, lysine endopeptidase, ARG-C, ASP-N, V8, or other enzyme known to artisans) or chemical reagents (such as cyanogens bromide or the like) as is performed during a global proteomics experiment. Liberated peptides can be separated using high performance liquid chromatography (HPLC) methods, such as, e.g., one dimension reversed phase, multiple dimensions in which two or more orthogonal dimensions of separation can be coupled to separate such complex mixture of peptides, and combinations thereof. Ultimately, separated peptide mixtures are co-deposited with a MALDI matrix onto a MALDI plate, or directly mixed with MALDI matrix, and deposited onto a MALDI plate as is practiced in the art of LC MALDI. Resultant samples are analyzed by MALDI-TOF-MS. One or more methods of the present teachings is then applied to identify putative phosphopeptides.

In various embodiments, phosphopeptide identification confidence can be increased by considering that the three forms of the peptide i.e., non-modified, phosphorylated (modified), and de-phosphate (de-modified), all bear the same amino acid sequence, but differ in regard to the degree of modification (e.g., phosphorylation). Therefore, confidence in phosphopeptide identification, can be increased by acquiring an MS/MS spectra for MS peaks corresponding to two or more of these three peptide forms to provide at least a partial sequence of each peptide form so analyzed, and performing a database search using these sequences, taking into account possible phosphorylation sites. A commercially available database that can be used for performing such searches is MASCOT® (Matrix Sciences Ltd.)

Sequencing peptides by tandem mass spectrometry (MS/MS) is typically achieved by selecting the molecular ion of a peptide (often referred to as "the precursor ion" or "parent ion") with a first mass spectrometer (often referred to as the first dimension of mass spectrometry) and directing the precursor ion into an ion fragmentor (such as, e.g., a collision cell were it collides with an inert gas). The precursor ion is fragmented in the collision cell to a series of fragment ions (often referred to as "daughter ions"), among which are a ladder of ions with sequentially decreasing numbers of amino acids. Two prominent sets of ions are typically produced. One is a sequence ladder with amino acid deletions from the C-terminal end of the peptide. Another is a ladder with amino acid deletions from the N-terminal end. The fragment ions are then typically directed into a second mass spectrometer (often referred to as the second dimension of mass spectrometry) to resolve the fragmentation pattern of the precursor ion, i.e., the selected peptide.

For example, many database search approaches first identify database peptides with a mass matching that of the precursor under consideration. The next step is to match the precursor's MS/MS spectrum to theoretical MS/MS spectra of the database peptides. Generally, the closest match is declared the winner. Modifications to peptides, e.g., phosphorylation, glycosylation, sulfation etc., can be taken into account in the database search, e.g., by addition of the expected mass of the modifying moiety to those peptides on which such modification generally occurs. Phosphorylation generally occurs on serine, threonine and tyrosin. and can be taken into account by adding the expected mass of the phosphorylation (80 u) to the mass of the database peptides prior to identifying putative matches (hits). Then, a plurality of potential matches can be formed for each hit by phosphorylating each of the serine, threonine and tyrosin sites prior to forming the theoretical spectra.

This process can be repeated when searching for a match to the de-phosphate peptide precursor. Instead of adding the phosphorylation mass (80 u) to the database peptide, the mass of the lost water molecule (18 u) is subtracted from the unmodified peptide's mass. Similar to the phosphorylation-related search, each of the serine, threonine and tyrosin site can be de-phosphated prior to forming the theoretical spectra. Similarly, a database search can be performed on the precursor for the peak corresponding to the unmodified peptide. In various embodiments, if all three searches yield a peptide with the same amino acid sequence, the confidence in the search result can be significantly increased.

Figure 7:
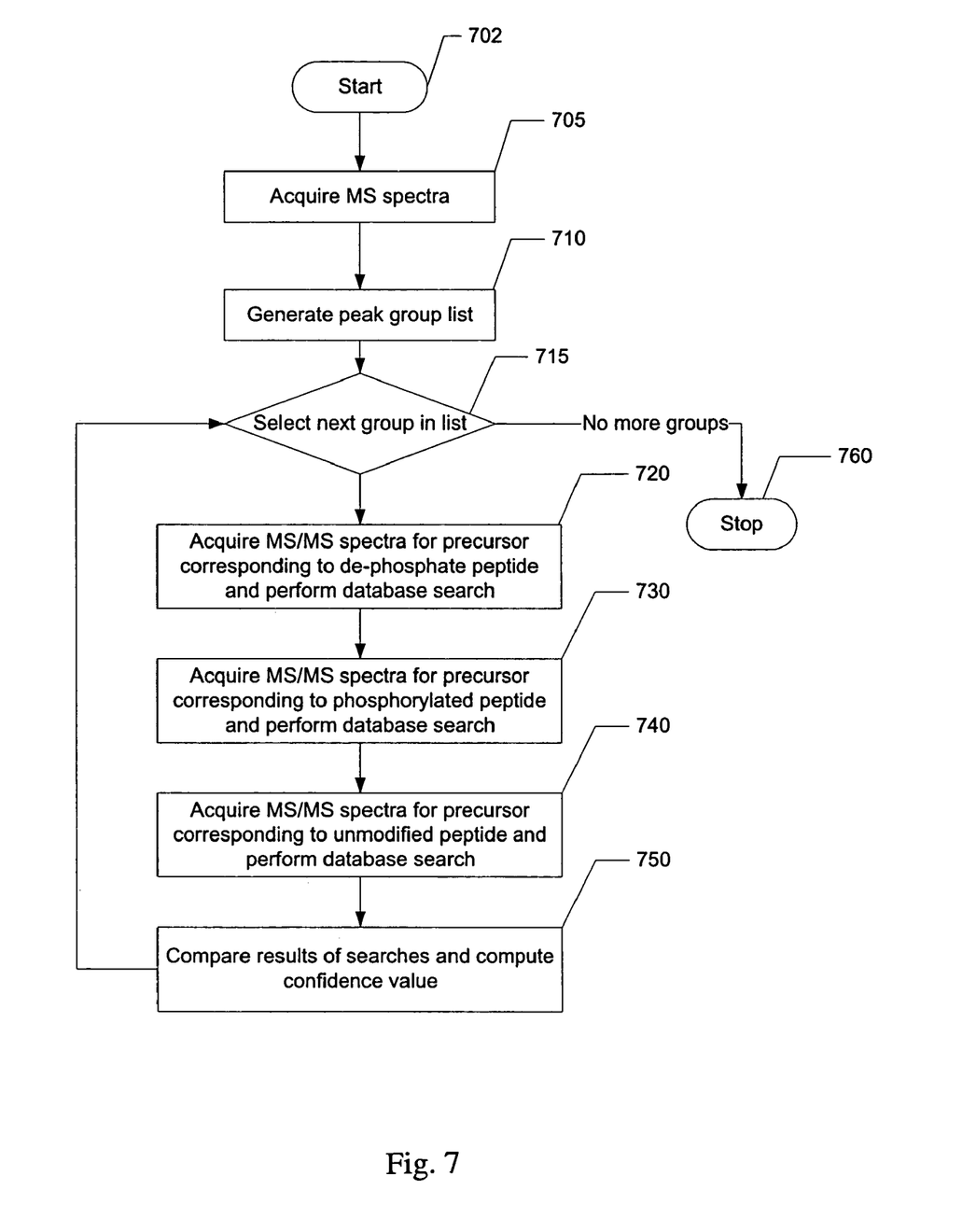
FIG. 7 depicts a flow chart of various embodiments of the current teachings that can be used for increasing confidence of detected peptides.

FIG. 7 illustrates a flowchart of various embodiments of the current teachings. At 705 a MS scan is performed. This scan can then be searched for peak relationships corresponding to the phosphorylation or other peptide modifications, e.g., glycosylation and sulfation. Phosphorylation can be present, for example, if there are peaks that are 18 u lower and 80 u higher than the current peak. In this way, groups of the peaks corresponding to a de-phosphate (de-modified) peptide, its corresponding non-modified peptide and its corresponding phosphorylated (modified) peptide can be formed (710). The process can proceed by acquiring an MS/MS spectra for the de-phosphate peptide precursor and searching the database taking into account the loss of the water molecule (720). A similar acquisition and search can be performed for the precursor corresponding to the phosphorylated peptide (730). And an acquisition and search can be performed for the non-modified peptide (740). Finally, the results of two or more of the searches can be compared to identify a common peptide (750). Additional control logic can be added (702, 715, 760) in order to process multiple groups in a list.

One skilled in the art will appreciate that any two of the three acquisition/search steps can be used and that the order of the acquisition/searches steps is generally not significant. As well, the exact type of database search algorithm is generally not important so long as it permits taking into account the various modifications. Some embodiments will compute the confidence in the result by accounting for differences in the ranking of the search results in each of the steps. For example, if two of the three searches produce a common peptide with a high score and the same peptide in the third search has a low score, the final confidence in the result may be lower than if all three searches yielded a common peptide with a high score.

Figure 8:
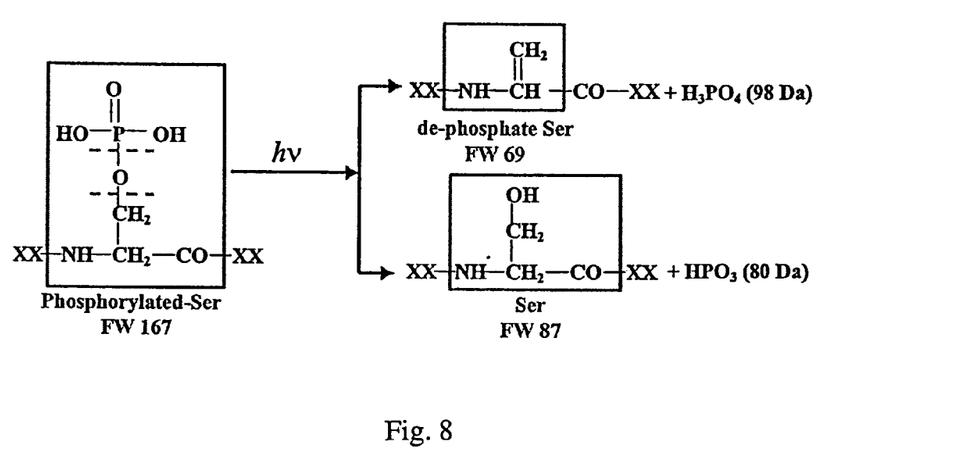
FIG. 8 schematically depicts phosphorylated serine (modified peptide) and its dissociation into a de-phosophate serine (de-modified peptide) and serine (non-modified peptide).

FIG. 8 schematically illustrates the dissociation of a phosphorylated serine peptide 802 (modified peptide) with a formal residue mass of about 167 u. When irradiated with light (hv), this can lead to fragmentation to produce: (i) de-phosphate serine 804 (the de-modified peptide corresponding to the modified peptide) with a formal residue mass of about 69 u and a $H_3PO_4$ moiety (expected mass of about 98 u), and/or (ii) serine 806 (the non-modified peptide corresponding to the modified peptide) with a formal residue mass of about 87 u and a $HPO_3$ moiety (expected mass of about 80 u).

Aspects of the present teachings may be further understood in light of the following examples, which should not be construed as limiting the scope of the present teachings in any way.

EXAMPLES

Example 1

Formation of Metastable Ions within a MALDI-TOF Mass Spectrometer

Figure 1:
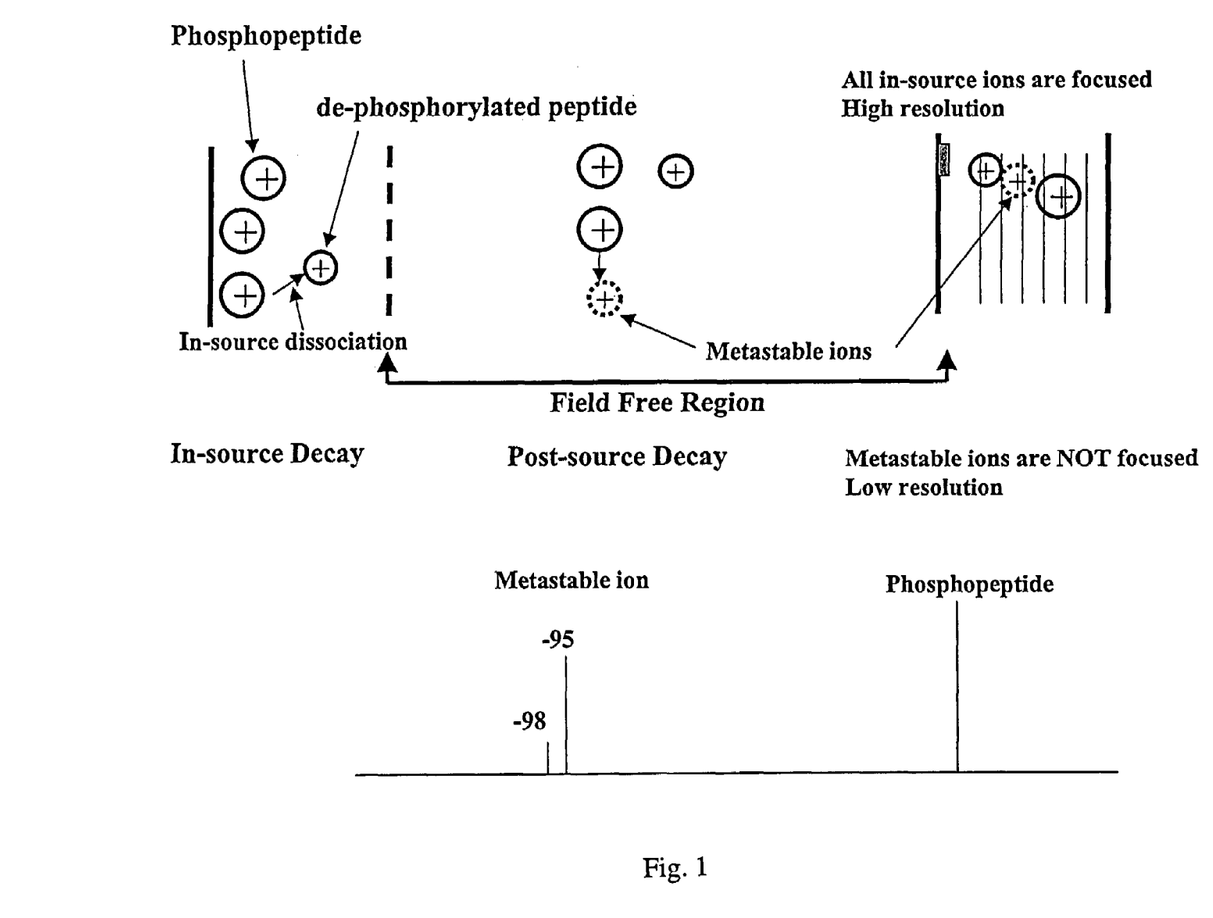
FIG. 1 depicts a schematic that highlights metastable ion formation in a MALDI-TOF mass spectrometer.

The schematic shown in FIG. 1 depicts a representation of the formation of metastable ions in a MALDI-TOF mass spectrometer. Here the ion represented by the smaller dashed circle formed in the field free region of the spectrometer is the metastable ion. As such, this ion will not be focused to the same extent as ions formed in the ion source region (as represented by the solid circles). Additionally, the ions formed in the field free region have increased kinetic energy spread from chemical bond dissociation, but the average of the gain in kinetic energy is zero. Both attributes can combine to result in a lower apparent resolution of this ion population, which helps to identify such metastable ions and ultimately, in various embodiments of the present teachings, the peptides from which they were generated.

Example 2

Figure 2:
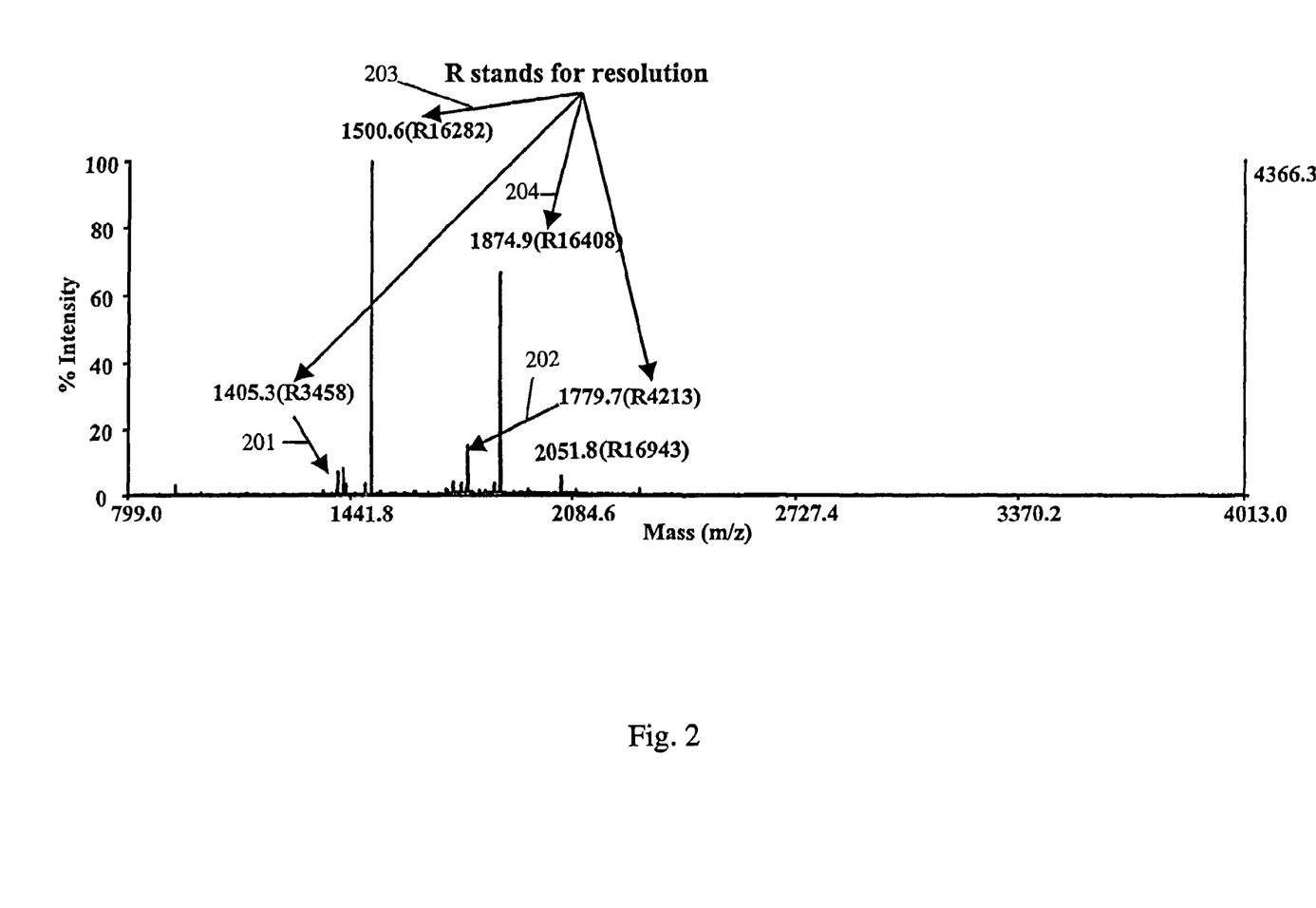
FIG. 2 depicts a MALDI-TOF-MS spectrum for a mixture of synthetically pure phosphopeptides LQRQPSpSPGPTPR (SEQ ID NO: 1), RYPRPVpSVPPSPSLSR (SEQ ID NO: 2), GTSFMMpTPYVVTRYYR (SEQ ID NO: 3) and CTNFM-MpTPpYVVTRYYR (SEQ ID NO: 4) in reflector mode of operation (note: a "p" to the left of an amino acid residue identifies the site of phosphorylation as the residue immediately to the right of the "p").

Detection of Metastable Ions in a Mixture of Phosphopeptides when Analyzed by MALDI-TOF-MS in Reflector Mode Operation A MALDI-TOF mass spectrum collected in reflector mode of operation of a sample containing phosphopeptides LQRQPSpSPGPTPR (SEQ ID NO: 1), RYPRPVpS-VPPSPSLSR (SEQ ID NO: 2), GTSFMMpTPYVVTRYYR (SEQ ID NO: 3) and CTNFMMpTPpYVVTRYYR (SEQ ID NO: 4) on an Applied Biosystems 4700 Proteomics Analyzer is shown in FIG. 2. The spectrum was an average of 20 sub-spectra for a total 1000 laser shots per spectrum. As seen across the mass range (900-2500), the observed resolution for most peptides is over 10,000. However, the mass resolution of certain ions is much lower (e.g., the ion at a m/z value of 1405.3 (201) was measured with a resolution of 3458 and the ion at a m/z value of 1779.7 (202) was measured with a resolution 4213). These poorly resolved peaks represent metastable ions. Both of these metastable ion associate peaks have corresponding modified peptide peaks about 95 u higher than themselves, and as such, these metastable ion peaks were identified as potentially originating from phosphorylated peptides. In this example the peak detected at m/z=1500.6 (203) was predicted to be a phosphopeptide corresponding the metastable ion detected at m/z=1405.3, and the peak detected at m/z=1874.9 (204) was predicted to be a phosphopeptide corresponding the metastable ion detected at m/z 1779.7.

Example 3

Confirmation that Peptide of m/z=1500.6 was a Phosphopeptide

Figure 3:
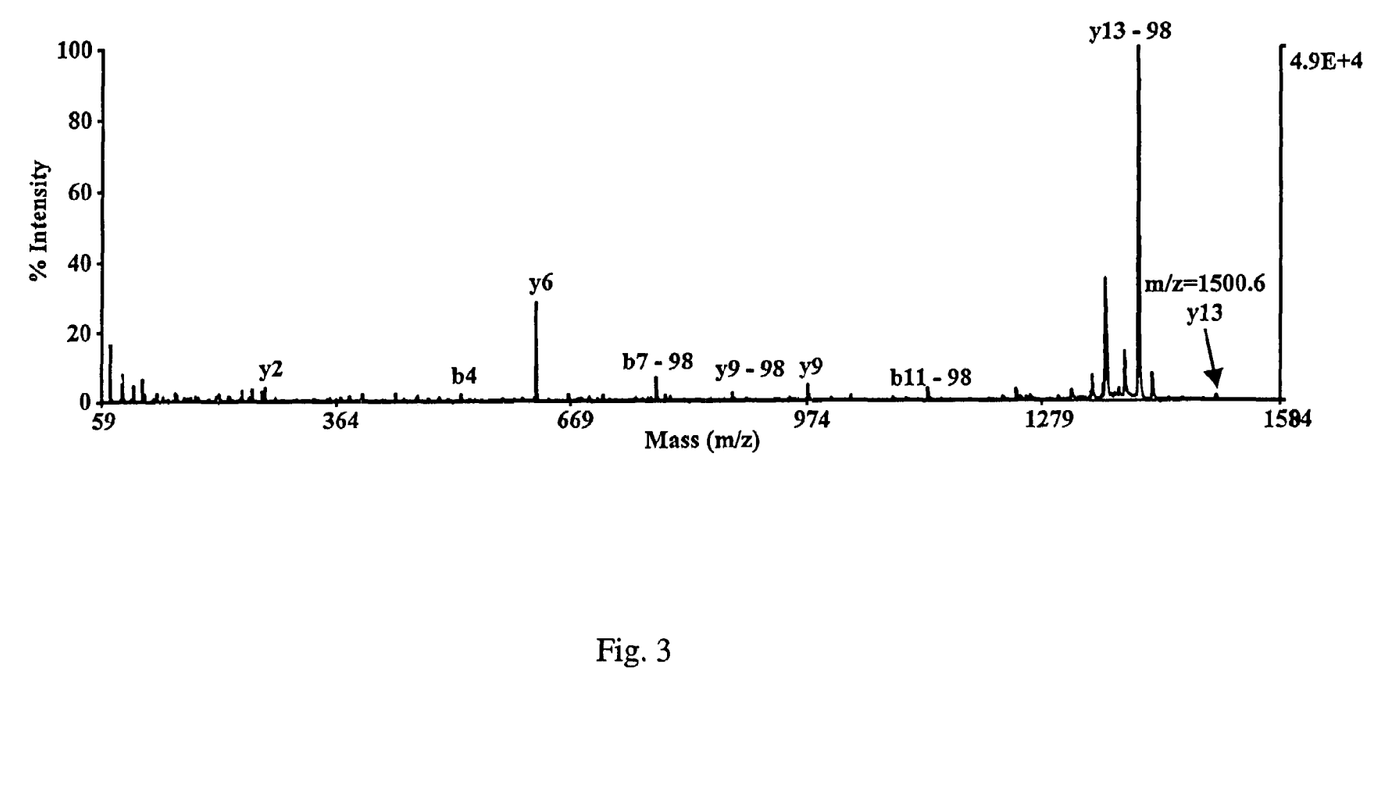
FIG. 3 depicts a MALDI-TOF-TOF spectrum for m/z=1500.6, a putative phosphopeptide identified by the detection of a metastable ion at m/z 1405.3 in the MALDI-TOF-MS spectrum shown in FIG. 2.

A MALDI-TOF/TOF spectrum for the ion detected at m/z=1500.6 was collected with an average of 25 sub-spectrum for a total 2500 laser shots per spectrum on an Applied Biosystems 4700 Proteomics Analyzer with high energy (1 Kev) collision induced dissociation and is presented in FIG. 3. This spectrum depicts the typical 98 u loss from the precursor ion and many of the y and b-series ions identified in this spectrum. This tandem MS (MS/MS) spectrum of m/z=1500.6 led to confirmation that this peptide was a phosphopeptide.

Example 4

Confirmation that Peptide of m/z=1874.8 was a Phosphopeptide

Figure 4:
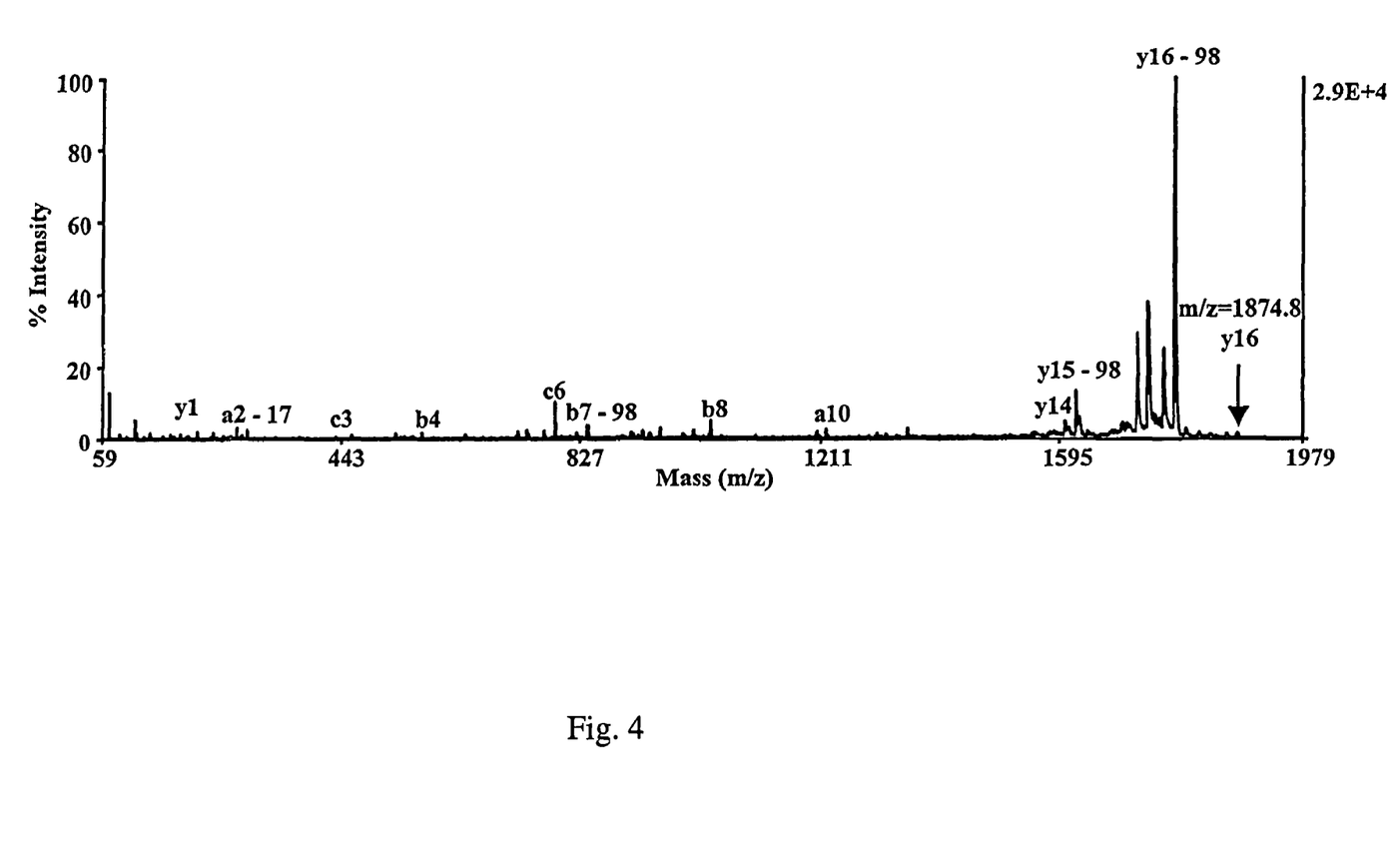
FIG. 4 depicts a MALDI-TOF-TOF spectrum for m/z=1874.8, a putative phosphopeptide identified by the detection of a metastable ion at m/z 1779.7 in the MALDI-TOF-MS spectrum shown in FIG. 2.

A MALDI-TOF/TOF spectrum for the ion detected at m/z=1874.8 was collected on an Applied Biosystems 4700 Proteomics Analyzer with high energy collision induced dissociation and was an averaged of 25 sub-spectrum for a total 2500 laser shots per spectrum and is presented in FIG. 4. This spectrum depicts the typical 98 u loss from the precursor ion and many of the y and b-series ions identified in this spectrum. This tandem MS (MS/MS) spectrum of m/z=1874.8 led to confirmation that this peptide was a phosphopeptide.

Example 5

Detection of Metastable Ions in a Trypsin Digest of α-casein when Analyzed by MALDI-TOF-MS in Reflector Mode Operation The phosphorylated protein, α-casein, was cleaved into fragments by an enzyme, bovine trypsin. These fragments are tryptic peptides which mean that all the peptides have either lysine or arginine at their C-terminus. These fragments are either non-phosphorylated peptides or phosphorylated peptides. This sample was mixed with MALDI matrix, α-cyano-4-hydroxylcinnamic acid, and was spotted on MALDI plate using a dry-droplet method. A MALDI-TOF reflector MS spectrum of an in-solution trypsin digest of this protein was collected on an Applied Biosystems 4700 Proteomics Analyzer with an average of 20 sub-spectra for a total 1000 laser shots per spectrum and is presented FIG. 5. A method using the metastable ion signal to identify a modified peptide, here a metastable ion signal of a phosphorylated peptide where an adjusted mass difference of 95 u was added to the mass-to-charge value of the metastable ion was applied to analysis of the trypsin digest of α-casein. In this example the method implemented successfully determined 3 potential phosphopeptides VPQLEIVPNpSAEER (SEQ ID NO: 6), YKVPQLEIVPNpSAEER (SEQ ID NO: 7), KYKVPQLEIVPNpSAEER (SEQ ID NO: 8), whereas a peptide mass fingerprinting (PMF) experiment only identified 2 phosphopeptides, VPQLEIVPNpSAEER, YKVPQLEIVP-NpSAEER, with one missed cleavage site in the MASCOT database search. An example is that the method identified a peak at 1952.0 (501) as a phosphopeptide whose sequence is YKVPQLEIVPNpSAEER. This peptide sequence was confirmed by a peptide mass fingerprinting using a MASCOT database search.

Example 6

Detection of Metastable Ions in a Phosphopeptide when Analyzed by Voyager STR MALDI-TOF-MS in Reflector Mode Operation A method of the current teachings using the adjusted mass difference was applied to analysis of a phosphorylated peptide precursor ion DLDVPIPGRFDRRVpSVAAE (SEQ ID NO: 5) on another type of MALDI-TOF mass spectrometer of Applied Biosystems, the Voyager STR. In the method using the metastable ion signal to identify a modified peptide, an adjusted mass difference of 94 u was added to the mass-to-charge value of the metastable ion. The spectrum of this phosphopeptide was collected on an Applied Biosystems Voyager DE™ STR with an average of 200 laser shots per spectrum and is presented in FIG. 6. In this example the method implemented by the algorithm successfully determined the presence of the phosphopeptide at 2191.7544 (601) and the ion at 2097.8196 (602) is a metastable ion.

Example 7

Continuation of Detection of Metastable Ions in a Phosphopeptide

Figure 9:
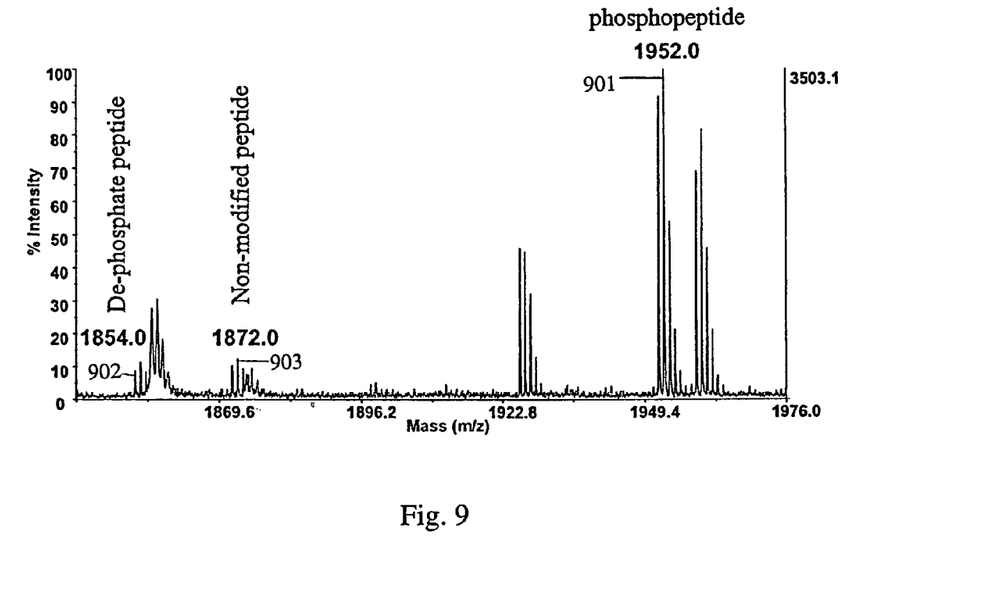
FIG. 9 is a mass spectrum of the tryptic digest of a phosphoprotein, α-casein.
Figure 10:
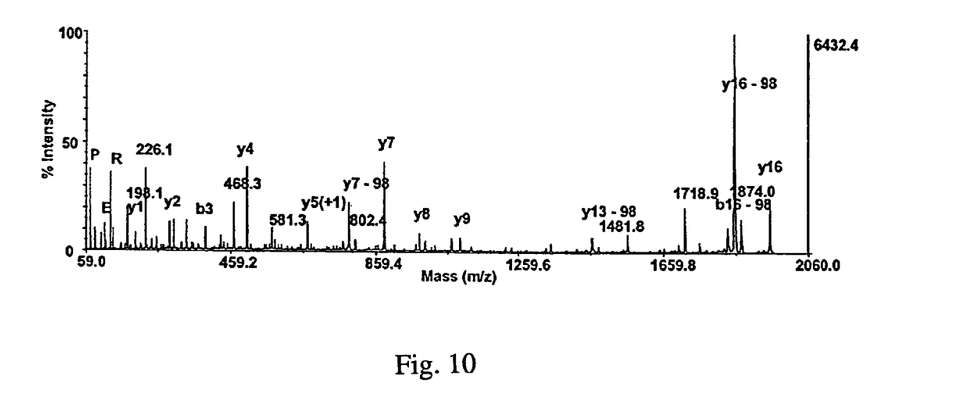
FIGS. 10 and 11 depict MS/MS spectra of various peaks in the mass spectrum of FIG. 9.
Figure 11:
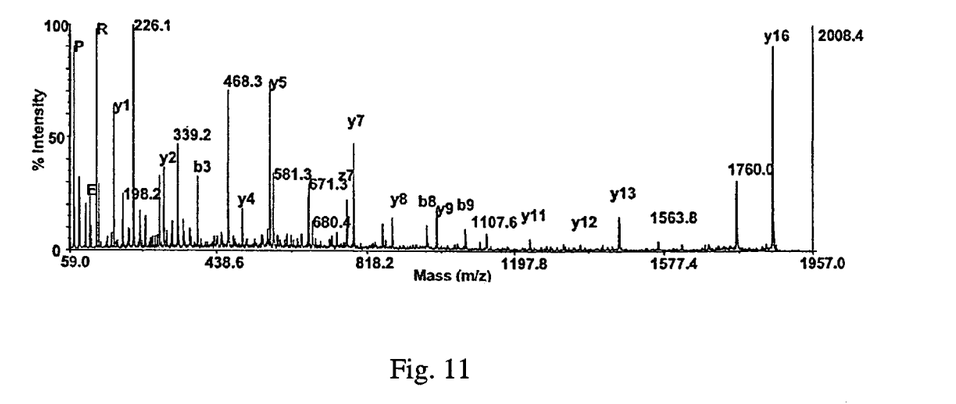

The phosphorylated protein, α-casein, was cleaved into fragments by an enzyme, bovine trypsin, and subject to mass spectrometry analysis using an Applied Biosystems 4700 Proteomics Analyzer to produce the spectrum shown in FIG. 9. A method using the metastable ion signal to identify a modified peptide, here a metastable ion signal of a phosphorylated peptide where an adjusted mass difference of 95 u was added to the mass-to-charge value of the metastable ion, identified a putative phosphopeptide at 1952.0 u (901) and its de-phosphate peptide was at 1854.0 u (902) and the non-modified peptide was at 1872.0 u (903). To confirm these findings, an MS/MS spectrum (FIG. 10) was taken with the putative phosphopeptide (1952.0 u) as the precursor ion that was fragmented. The resultant MS/MS spectrum was subjected to a MASCOT database search using variable phosphorylation of serine, threonine and tyrosine. The peptide ion score from the MASCOT search was 50 and its confidence of identification was 99.7%. Another MASCOT database search was conducted of the MS/MS spectrum of the de-phosphate peptide (1854.0 u), but this time using de-$H_2O$ as the variable modification of serine, threonine and tyrosine. The results are shown in FIG. 11. In this instance, the peptide ion score was 85 and its confidence of identification was 100%. The peptide sequence found in both data base searches was the same, and thus, this example shows that the precursor phosphopeptide found at 1952.0 u was confirmed to be a phosphorylated peptide.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings are described in conjunction with various embodiments, it is not intended that the present teachings be limited to such embodiments or examples. On the contrary, the present teachings encompass various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

The invention claimed is:

1. A method of identifying the presence of a modified peptide in a mixture of peptides by a mass spectrometry instrument comprising the steps of:
   generating a mass spectrum of a mixture of peptides, the mass spectrum comprising a plurality of peaks over a selected range of mass-to-charge values;
   determining a resolution value for at least a portion of the peaks within the range of mass-to-charge values;
   setting a peptide resolution value based at least on the determined resolution value;
   selecting one or more peaks with a resolution lower than the peptide resolution value as a putative metastable ion of a modified peptide;
   deriving an adjusted mass difference for a chemical moiety modifying a peptide, wherein the mass of the chemical moiety is the difference between the mass of a precursor ion of a modified peptide and a corresponding metastable ion, and wherein the deriving an adjusted mass difference takes into consideration instrument geometry as:

$$\Delta m_{amd} = 2\beta \Delta m - \beta^2 \frac{\Delta m^2}{m}$$

where $\Delta m_{amd}$ is the derived adjusted mass difference, $\beta$ is a constant that depends on geometry of the instrument; $\Delta m$ is the mass of the chemical moiety, and m is a mass value falling within the selected range of mass-to-charge values,
   adding the derived adjusted mass difference to the mass-to-charge value of the selected peak corresponding to the putative metastable ion to derive an empirical mass-to-charge value for the precursor ion of the modified peptide; and
   identifying that a modified peptide is present in the mixture of peptides if a peak exists in the mass spectrum at about the empirical mass-to-charge value.

2. An article of manufacture comprising a computer-readable media with computer readable instructions embodied thereon for performing the method of claim 1.

3. The method of claim 1, wherein the modified peptide is a phosphorylated peptide.

4. The method of claim 3, wherein the moiety is H3PO4.

5. The method of claim 1, wherein the modified peptide is one or more of a glycosylated peptide and a sulfonated peptide.

6. The method of claim 1, wherein m, the mass value falling within the selected range of mass-to-charge values, is an average value of an upper value of mass and a lower value of mass in the selected mass-to-charge range.

7. A method of identifying the presence of a modified peptide in a mixture of peptides by mass spectrometry comprising the steps of:
   generating a mass spectrum of a mixture of peptides; said mixture of peptides falling within a selected range, wherein the selected range is bounded by a first mass $m_1$, and a second mass $m_2$;
   identifying a putative metastable ion peak in the mass spectrum, said putative metastable ion peak having a resolution lower than a determined resolution value for peaks in the selected range, wherein the putative metastable ion peak has a mass $m_{pmi}$;
   deriving an average adjusted mass difference between a modified peptide and a metastable ion over the selected range of mass values, wherein deriving the average adjusted mass difference takes into consideration instrument geometry as:

$$\Delta \overline{m}_{amd} = \Delta m_{amd1} + \Delta m_{amd2}/2; \text{ given}$$

$$\Delta m_{amd1} = 2\beta \Delta m - \beta^2 \frac{\Delta m^2}{m_1}; \text{ and}$$

$$\Delta m_{amd2} = 2\beta \Delta m - \beta^2 \frac{\Delta m^2}{m_2}$$

where, $\Delta \overline{m}_{amd}$ is the average derived adjusted mass difference over the selected range of masses, $\Delta m_{amd1}$ is a first adjusted mass difference for a first mass $m_1$ in the selected range, $\Delta m_{amd2}$ is the second adjusted mass difference for a second mass $m_2$ in the selected range, $\beta$ is a constant that depends on geometry of the instrument, and $\Delta m$ is a mass of a dissociated chemical moiety modifying the peptide;
   calculating an empirical mass value for a modified peptide, wherein the calculation is given by, $m_{mp} = \Delta \overline{m}_{amd} + m_{pmi}$ where $m_{mp}$ is the derived empirical mass for the modified peptide, $\Delta \overline{m}_{amd}$ is the average derived adjusted mass difference over the selected range of masses, and $m_{pmi}$ is the mass of the putative metastable ion peak; and
   identifying that a modified peptide is present in the mixture of peptides if a peak exists in the mass spectrum at about the empirical mass value.

* * * * *